(12) United States Patent
McDaniel

(10) Patent No.: US 8,067,470 B2
(45) Date of Patent: Nov. 29, 2011

(54) LINOLEIC ACID PREPARATIONS FOR THE TOPICAL TREATMENT OF MALE AND FEMALE PATTERN ANDROGENETIC ALOPECIA, AGE-RELATED ALOPECIA, AND KERATOSIS PILARIS

(76) Inventor: William Robert McDaniel, Franklin, TN (US)

( * ) Notice: Subject to any disclaimer, the term of this patent is extended or adjusted under 35 U.S.C. 154(b) by 98 days.

(21) Appl. No.: 12/012,198

(22) Filed: Feb. 1, 2008

(65) Prior Publication Data

US 2009/0197954 A1 Aug. 6, 2009

(51) Int. Cl.
*A61K 31/201* (2006.01)
(52) U.S. Cl. .................................. 514/560
(58) Field of Classification Search ............. 514/560
See application file for complete search history.

(56) References Cited

U.S. PATENT DOCUMENTS

| 5,443,844 | A | * | 8/1995 | McDaniel | 424/484 |
| 5,760,043 | A | * | 6/1998 | Dufetel et al. | 514/272 |
| 6,159,475 | A | * | 12/2000 | Olguin | 424/731 |
| 6,465,421 | B1 | * | 10/2002 | Duranton et al. | 514/1 |

FOREIGN PATENT DOCUMENTS

EP 0309086 A1 * 3/1989

OTHER PUBLICATIONS

University of Maryland Medical Center (UMMC) [online], www.umm.edu, Jun. 2006 [retrieved on Dec. 16, 2008]. Retrieved from the Internet: <URL: http://www.umm.edu/altmed/articles/alopecia-000004.htm.*
Atopic Dermatitis [online], www.helpforkp.com, Jan. 1999 [retrieved on Dec. 17, 2008]. Retrieved from the Internet: <URL: http://www.helpforkp.com/atopic_dermatitis.html.*
Lautenschläger (Kosmetische Praxis, vol. 6, pp. 6-8; 2004).*
MaleHealth.com ([Retreived online on Nov. 4, 2009]. Retrieved from the Internet: <URL: http://www.malehealth.co.uk/userpage1.cfm?item_id=122).*
Merck Manual ([Retreived online on Nov. 4, 2009]. Retrieved from the Internet: <URL: http://www.merck.com/mmhe/sec18/ch203/ch203m.html?qt=keratosis%20pilaris&alt=sh).*
Jaworsky et al. (British Journal of Dermatology, vol. 127, Issue 3, Abstract; Sep. 1992).*
Kersey et al. (British Journal of Dermatology, vol. 103, Issue 6, Abstract; Dec. 1980).*
TheFreeDictionary.com reference [Retrieved on Feb. 14, 2011 from the Internet: <URL: http://medical-dictionary.thefreedictionary.com/sebaceous+follicle].*
Plewig et al. ["The Anatomy of Follicles" in: Acne: Morphogenesis and Treatment (Springer-Verlag, New York, 1975), p. 2-5, 52, 53, 122 and 123].*
Montagna et al. ["The Pilary Apparatus" in: The Structure and Function of Skin (Academic Press, New York, 1974), p. 172-175, 218-221, 242-247, 250 and 251].*
Olsen ["Pattern Hair Loss in Men and Women" in: Disorders of Hair Growth (McGraw-Hill Medical Publishing Division, New York, 2003), p. 323].*
Pinkus et al. ["Inflammation Involving the Pilosebaceous Complex" in: A Guide to Dermatohistopathology (Appleton-Century-Crofts, New York, 1976), p. 263 and 264].*

* cited by examiner

*Primary Examiner* — Jeffrey S. Lundgren
*Assistant Examiner* — Nelson Blakely, III

(57) ABSTRACT

A preparation for the topical application of linoleic acid to treat male and female androgenetic alopecia, age-related alopecia, and keratosis pilaris contains between about 0.1% and about 10%, preferably between about 1% and about 5%, and specifically about 2% linoleic acid by volume in its carrier vehicle. This acts to correct the local linoleic acid deficiency that exists in the follicles in these conditions and provides linoleic acid to suppress growth of *Propionibacterium acnes* with resultant reduction in its porphyrin production which in turn reduces microinflammation and altered keratinization that damages follicles and eliminates functioning follicles in alopecia and causes follicle plugging in keratosis pilaris.

12 Claims, No Drawings

LINOLEIC ACID PREPARATIONS FOR THE TOPICAL TREATMENT OF MALE AND FEMALE PATTERN ANDROGENETIC ALOPECIA, AGE-RELATED ALOPECIA, AND KERATOSIS PILARIS

This invention relates to linoleic acid preparations for topical application in the treatment of androgenetic pattern scalp alopecia in human males and females and treatment of age-related alopecia and keratosis pilaris.

The human species, *Homo sapiens* represents the highest order of the mammalian kingdom and therefore man shares with all of his lower mammal relatives the trait of having his entire body covered with hair. While offering the obvious benefit of insulating the body, hair also has the characteristic distribution, texture, and color, that permits visible recognition and separation of one species from another. In most mammals, body hair growth continues throughout life even though changes in its color and density may occur seasonally or with aging. Only in the two highest orders of mammals, apes and humans, do specific patterns of hair loss (alopecia) develop on the scalps of a percentage of the younger members, both males and females. Also, at least in humans, it has long been recognized that even in completely healthy men and women who do not have pattern alopecia a gradual reduction in the number of scalp hairs occurs beginning after the third decade of life.

Human scalp pattern alopecia in both males and females has been established to be a genetic trait. The generally-accepted incidences of the condition in the population are 55% among males and 15% among females. The earliest signs of the development of pattern alopecia occurs at puberty in both sexes but men usually have more accelerated decrease in hair density than women until after women undergo the decreased ovarian production of estrogen at menopause. This pattern was well recognized even prior to the proof by Hamilton in 1942 that the androgen hormone testosterone causes the changes that lead to pattern alopecia. He studied a population of eunuchs (castrated males) and found that none of them who lost their testicular function prior to puberty developed male pattern alopecia and that administration of testosterone to them caused hair loss but only in those who had a family history of alopecia.[1] The inheritance pattern has been studied extensively and is generally accepted as being autosomal dominant with variable penetrance. Further confirmation of the causative role of androgen hormones such as testosterone has come from the finding of acceleration of male pattern alopecia in male athletes using such hormones as anabolic agents for increasing muscle mass or athletic performance. Women who suffer from disorders of hormone imbalance such as polycystic ovarian syndrome where androgens such as androstenedione or dihydroepiandrosterone (DHEA) are abnormally elevated often develop pattern alopecia. Women who are genetically programmed to develop pattern alopecia often have acceleration of the condition at menopause when estrogen produced by the failing ovaries is no longer available to predominate over adrenal androgens. Because of the aforementioned proven connections of pattern scalp alopecia to both hormones and genetic factors, the term androgenetic alopecia (AGA) has become recognized as the most appropriate name for the condition.

[1] Hamilton, J B, "Male hormone stimulation is a prerequisite and an incitant in common baldness", American Journal of Anatomy, Vol. 71, p. 451, 1942.

In humans, hair on the scalp does serve the function of insulation from cold and blocking out some of the harmful ultraviolet radiation from the sun an upright species is exposed to, but in actuality the presence or absence of the normal pattern of scalp hair cover has become a far greater concern from the aesthetic sense. Men and women idolize as their visual ideals the men and women who have perfectly-groomed full heads of hair. While the majority of men have come to accept baldness as a fact of life, billions of dollars are still spent annually on hair growth potions, hair transplantation, or artificial hair replacement devices. Women generally view alopecia as much more unacceptable on themselves than on men and therefore also spend vast sums on similar efforts at correction or camouflage of the problem.

With such a vast potential economic windfall to be gained from the sale of any safe product that could reverse the hair loss and return hair to the scalps of these millions of affected men and women, researchers have worked hard toward developing such a compound. Realizing that castration of the male population, while effective, would never be a logical solution and treating all post-menopausal women with massive levels of estrogen for hair growth alone would be quite dangerous, efforts of scientific and pharmaceutical researchers has focused more on treating the scalp itself specifically rather than the entire body. After the first successful hair transplantation by Orentreich in 1970 proved that hair from parts of the male scalp other than the areas of alopecia would grow indefinitely after being transplanted into the bald area, efforts to study the differences in growth and metabolism of hairs from different parts of the scalp became the focus. This research led to the elucidation of androgen receptors on the hair follicles and subsequently to in vitro studies of androgen binding and enzyme differences between scalp areas. The present level of understanding points to genetic differences in the levels of two enzymes, aromatase and 5-alpha reductase as the determining factor in whether or not an area of scalp retains or loses hair. Aromatase causes the conversion of androgens to estrogenic compounds that encourage hair growth and retention. 5-alpha reductase converts testosterone and other androgens to the super-potent androgen dihydrotestosterone (DHT) which binds tightly to the androgen receptor and through a mechanism heretofore not fully elucidated causes a progressive shrinkage of scalp follicles that eventually results in cessation of hair growth.

Two compounds, minoxidil and finasteride, have been developed and proven to cause regrowth of hair in a percentage of patients treated for AGA. Minoxidil, a potent vasodilator used initially to treat severe hypertension, was found to induce excessive hair growth as an undesirable side effect in a significant percentage of patients receiving the drug orally. That capability was exploited through use of a topical formulation of the compound in a 2-5% concentration that indeed results in modest regrowth of scalp hair in some patients after six months of application. The mechanism of action has never been elucidated fully but has been speculated to be due minoxidil blocking intracellular production of enzymes or substrates that cells might produce as a result of being told to stop growing by binding of DHT to their androgen receptors.[2] Vasodilation has been ruled out as the mechanism because that effect of the drug is quite transient. The discovery of finasteride, a compound that blocks 5-alpha reductase conversion of testosterone to the more potent DHT, was met with great excitement in the scientific and financial world. This compound proved to block only the form of the 5-alpha reductase enzyme found in prostate and scalp tissues, making it quite specific and also safe enough to get FDA approval for treatment of male pattern AGA. This drug also had the relative advantage of the oral route of administration, thus avoiding the messiness and inconvenience of twice-daily applications of topical minoxidil. Studies proved that 95% of recipients lost less scalp hair after one month and that 67% began regrowing lost hairs after six months. This medication has been the best and most frequent medical treatment of AGA for the past fifteen years since it became available, even though it is quite expensive and not all recipients show a response.

2 Rietchel, R L M D, "Androgenetic Alopecia: Treatment with Minoxidil", in Symposium on Alopecia, Howard P. Baden, editor, New York: HP Publishing Co., 1989, pp. 1-10.

During the fifteen years since finasteride has been available, the question that has challenged researchers has been why, if it so effectively inhibits 5-alpha reductase conversion of testosterone to DHT, do 35% or more of balding recipients show poor or no response. Around 1992 it began to be recognized that microscopic analysis of hair follicles undergoing miniaturization and loss of function in AGA exhibit signs of a perifollicular inflammatory reaction around the upper portion (infundibulum) of the follicle that is quite distinct from other causes of hair loss such as alopecia areata that are known to be autoimmune in nature.[3] In fact, the inflammation appears by the time the first signs of hair shaft miniaturization are evident and continues to be present in the area of the dermis and subcutaneous tissue even after the original full size and length follicle gradually shrinks and shortens leaving behind concentric layers of fibrous tissue. Follicles eventually shrink to the point that only non-growing colorless (vellus) hairs are present in the shallow ones that remain. The inflammation does not leave even these end-stage functionless follicles. Studies done to characterize this inflammation have revealed that the cells consist of activated T-lymphocytes, mast cells, and macrophages. Staining with immunofluorescent reagents has shown immunoglobulin M and complement C3 located in the follicular basement membrane zone and also in the fibrotic layers that form around the shrinking follicles in 96% of alopecia patients and only in 12% of subjects without alopecia.[4] The inflammatory cytokine interleukin-1 has been identified within these active areas of inflammation also. Because this inflammation does not result in visible redness or any of the usual clinical signs that accompany it, the term microinflammation has been used to describe it.

3 Jaworsky, C., et al., "Characterization of Inflammatory Infiltrates in Male Pattern Alopecia: Implications for Pathogenesis", British Journal of Dermatology, Vol. 127 (#3), pp. 239-246, 1992
4 Young, J W et al., "Cutaneous Immunopathology of Androgenetic Alopecia", Journal of the American Osteopathic Assn., Vol. 91 (#8), p. 765, 1991.

The elucidation of the probable stimulus for this microinflammation and the concept of a topical compound that can suppress it safely and can result in slowing and even reversing the process of AGA is the focus of the present invention.

Microbiologic studies have shown that after puberty skin flora in hair follicles of oily skin areas such as the face and scalp is predominantly Propionibacterium acnes (P. acnes) with lesser presence of staphylococci and Malassezia species. P. acnes is an anaerobic bacterium that is well adapted for life in the sebum-rich, oxygen-free environment inside face and scalp follicles. Metabolically, it produces a number of compounds that can cause inflammation inside and around hair follicles. Lipase enzymes result in breakdown of inert triglycerides into inflammatory free fatty acids which disrupt facial and upper trunk follicles and cause the papules, pustules, and cysts seen clinically as acne. Cyanocobalamin (vitamin B12) is also produced and is a known aggravator of acne when it is administered orally to acne-prone patients. Most pertinent to the present invention is the production of tetrapyrrole porphyrin compounds, especially coproporphyrin III, which are inflammatory by nature but are especially inflammatory when excited by their specific absorption of ultraviolet light in the 300-450 nanometer wavelength range which is abundantly available in natural sunlight. Such activated porphyrins have been shown to cause deposition of immunoglobulins and complement as described in AGA follicles. Scalp follicles in areas of alopecia are often seen to exhibit auto-fluorescence in UV light indicating the active production of porphyrins in these follicles. This has led some authors to even suggest that the normal location of AGA on the vertex of the scalp more than on the sides could make the process in part a photo-aggravated one.[5] The end result of the follicular microinflammation, perifollicular fibrosis, and the miniaturization of normal follicles until they are non-functional could largely therefore be blamed on P. acnes, either through its production of inflammatory compounds or porphyrins or alternately due to antimicrobial peptides or other compounds produced locally as a defense mechanism against it. In any event, reduction of the population of P. acnes in scalp follicles can prevent inflammation and slow or reverse the process of miniaturization that causes AGA and baldness.

5 Trueb, R M, "Is Androgenetic Alopecia a Photoaggravated Dermatosis", Dermatology, Vol. 207, pp. 343-348, 2003.

The circumstance that connects increased androgen activation locally in balding areas with inflammation and fibrosis due to P. acnes is hereby proposed to be the reduction in linoleic acid concentration in sebum which is overproduced as a direct result of DHT stimulation. The environment that develops in AGA scalp is that of a localized essential fatty acid deficiency in the affected follicles much like that demonstrated to exist in facial acne follicles by Downing et al.[6] The superpotent androgens produced by increased 5-alpha reductase activity in genetically-determined areas of scalp stimulate such an overproduction of sebum that the essential fatty acid linoleic acid becomes insufficiently available because of its normally limited supply, resulting in sebum that is deficient in this protective fatty acid. This localized essential fatty acid deficiency results in a number of changes which together produce the stunted, functionless follicles typical of AGA. As established through prior art by this inventor, linoleic acid in normal concentration in sebum prevents growth of P. acnes.[7] Patients with systemic essential fatty acid deficiency states due to malabsorption or improper parenteral nutrition have in fact been noted to have hair loss in addition to dry, exfoliating skin. Studies in these patients have demonstrated a striking loss of normal epithelial barrier function as well as increased and altered keratinization of surface and follicular epidermis, and such a change could permit inflammatory compounds such as porphyrins and vitamin B12 produced by P. acnes to penetrate the epithelium and elicit the microinflammation discussed above that is postulated by this inventor to cause the eventual fibrosis and miniaturization of follicles that leads ultimately to the bald state of AGA.

6 Downing, D P PhD. et al., "Essential Fatty Acids and Acne", Journal of the American Academy of Dermatology, Vol. 14 (#2, part 1), pp. 221-225, 1986.
7 McDaniel, W R M D, "Linoleic Acid Preparations for the Topical Treatment of Acne Vulgaris", U.S. Pat. No. 5,443,844. Issued Aug. 22, 1995.

Studies have shown that topically-applied linoleic acid can replenish even the depleted levels seen in systemic essential fatty acid deficiency states, so it is merely academic to state that topical linoleic acid compounds can supply adequate amounts to correct the localized deficiency in scalp follicles in AGA. The prior art presented by this inventor showed that only a 2% concentration of linoleic acid is required to completely inhibit growth of P. acnes in culture. The difference between the clinical outcome of localized linoleic acid deficiency in scalp and facial follicles in AGA and acne, respectively, is quite probably due to the difference in the normal patterns of keratinization in follicles of the two areas. In the scalp, the infundibular keratinization when pathologically altered becomes permeable to inflammatory compounds leading to microinflammation, perifollicular fibrosis, and miniaturized non-functional follicles. Clinical signs of acne in facial follicles results from action of P. acnes-produced lipases on the microcomedo, which is the product of altered follicular keratinization caused by linoleic acid-deficient sebum in sebaceous follicles that rarely produce full-sized hairs in the normal individual.

The following examples are presented as evidence that a state of linoleic acid deficiency exists in scalp follicles affected by AGA and that correcting this deficit and the resultant reduction in P. acnes colonization and activity results in microscopic and clinical improvement in signs of the condition.

EXAMPLE 1

13-cis-retinoic acid, used for the past 25 years as the premier drug to control severe acne, has been shown to work by reducing sebaceous gland oil production and has been proven to cause a parallel and equal reduction in P. acnes counts in acne-prone skin.[8] Slowing oil production is accompanied by an increase in linoleic acid concentration to its normal level. Linoleic acid has been proven in vitro to prevent growth of P. acnes in culture at concentrations similar to the normal level found in follicles not influenced by DHT stimulation of oil production. This inventor has observed increased terminal (full sized) hair growth in the balding scalp of a 60 year-old man treated for five months for cystic acne with the medication.

8 Leyden, James J. M D et al., "Qualitative and Quantitative Changes in Cutaneous Bacteria Associated with Systemic Isotretinoin Therapy for Acne Conglobata", Journal of Investigative Dermatology, Vol. 86, 390-393, 1986.

EXAMPLE 2

A reduced linoleic acid level was measured in the sebaceous triglycerides derived from vertex scalp follicles in a group of adult men with AGA. Age-matched men without hair loss were found to have higher levels. The sample was not large enough for the demonstration of statistical significance.

EXAMPLE 3

In a study of subjects having male-pattern alopecia, the use of a microbicidal lotion reduced P. acnes colonization and in turn reduced the microscopic evidence of the microinflammation encountered in the follicles of AGA.[9]

9 Mahe, Y F PhD, et al., "Androgenetic Alopecia and Microinflammation", International Journal of Dermatology, Vol. 39(#8), p. 576, 2000.

Age-related hair thinning is a universal finding in human scalps beginning in the third decade of life. While this might be attributed to metabolic or hormonal factors associated with advancing age such as decreased circulation or lower growth hormone levels, it is more likely due to microbial factors secondary to changes in the fatty acid milieu in the follicle as proposed above for AGA. Studies of skin surface lipids have documented progressive reduction in the concentration of linoleic acid in scalp sebaceous lipids in all age groups tested beginning at puberty.[10] Restoring linoleic acid levels to normal through topical application could reasonably be expected to lead to better retention of scalp hair in the aging population through concomitant reduction in P. acnes-induced microinflammation as in AGA.

10 Nazzaro-Porro, Marcella MD, "Effects of Aging on Fatty Acids in Skin Surface Lipids", Journal of Investigative Dermatology, Vol. 73, pp. 112-117, 1979.

Keratosis pilaris is a localized cutaneous disorder exhibiting the finding of spiny follicular prominences and erythema (redness) on the upper arm, thigh, and shoulders of some pre-pubertal children, adolescents, and adults. In pre-pubertal children prior to hormonal stimulation of facial oil production, it can be seen transiently on the cheeks, typically the least oily part of the face. It is a hereditary trait and shows a correlation with a family or personal history of atopic diseases such as eczema, allergic rhinitis, and asthma. It has been demonstrated that such atopic individuals lack the enzyme, delta-6-desaturase, and that this deficiency causes defective metabolism of dietary essential fatty acids (linoleic acid and linolenic acid). This defect, as should be expected, shows effects on the skin in areas normally the least oily and these areas are the ones where keratosis pilaris is manifested. The histology is reminiscent of the intra-follicular hyperkeratosis and low-level microinflammation seen in AGA follicles, except that AGA scalp follicles are larger and have large sebaceous glands opening into them. It is likely that localized linoleic acid deficiency with resultant aberrations in keratinization and in inflammation, due to permissive changes in microflora such as P. acnes and yeasts, is its etiology. Topical linoleic acid preparations would therefore be a logical approach to the treatment of the condition. Topical linoleic acid in the form of an oil has in fact caused amelioration of both the roughness and redness of clinical keratosis pilaris in more than 20 patients with the condition treated by this inventor.

In the preferred embodiment of this invention, a topical preparation containing between 0.1% and 10% linoleic acid in a carrier lotion is to be applied in the amount of at least 1 cc about twice per day to scalp affected by AGA or age-related alopecia or skin areas affected by keratosis pilaris to correct the localized state of linoleic acid deficiency that alters follicular epithelial keratinization, resulting in the formation of hard follicular plugs in keratosis pilaris and a reduction in the follicle wall's barrier to penetration of interfollicluar inflammatory compounds produced by yeasts and bacteria in AGA and age-related alopecia. The applied linoleic acid normalizing the level of linoleic acid in the follicles also serves to inhibit the production by P. acnes of inflammatory compounds such as photoactive porphyrins and Vitamin B12 that create the microinflammation in and around the scalp follicles that ultimately leads to the perifollicular fibrosis, follicle miniaturization, and eventually functionless follicles seen clinically as localized baldness in AGA and progressive scalp hair thinning in age-related alopecia.

What is claimed is:

1. A method of treatment to reduce microinflammation that leads to follicle miniaturization in human scalp skin in adults affected by the genetically- and hormonally-induced condition of male and female androgenetic alopecia, consisting of the application of linoleic acid in a carrier vehicle to inhibit *Propionibacterium acnes*' production of photoactive and inflammatory porphyrins that cause micro inflammation, perifollicular fibrosis, and loss of viable and growing hair follicles, the linoleic acid being in a concentration of between 0.1% and 10% by volume.

2. A method of reducing the perifollicular microinflammatory process whereby all humans lose scalp hair increasingly with age due to the progressive diminution in linoleic acid concentration in scalp sebum seen with aging, consisting of the application of linoleic acid in a carrier vehicle in a concentration of between 0.1% and 10% by volume, a concentration sufficient to inhibit *Propionibacterium acnes*' production of inflammatory and photoactive porphyrins which cause the micro-inflammation and perifollicular fibrosis and eventual loss of functioning hair follicles.

3. A method of treating the inflammation that accompanies a keratosis pilaris condition, consisting of the application to affected areas of human skin of linoleic acid in a carrier vehicle in a concentration of between 0.1% and 10% by volume to normalize the diminished fatty acid and linoleic acid concentrations found in areas of skin exhibiting keratosis pilaris, thereby suppressing *Propionibacterium acnes*' production of compounds causing the low-level inflammation that accompanies the altered keratinization known to be characteristic of the condition.

4. The method of claim 1, 2, or 3, the concentration of linoleic acid in the carrier vehicle being between 1% and 5% by volume.

5. The method of claim 1, 2, or 3, the concentration of linoleic acid in the carrier vehicle being about 2% by volume.

6. The method of claim 1, 2, or 3, the linoleic acid in the carrier vehicle being applied to the skin in the amount of at least 1 cc about twice per day.

7. The method of claim 1, 2, or 3, said carrier vehicle being a lotion.

8. The method of claim 1, 2, or 3, said carrier vehicle being a cream.

9. The method of claim 1, 2, or 3, said carrier vehicle being a shampoo.

10. The method of claim 1, 2, or 3, said carrier vehicle being an oil.

11. The method of claim 1, 2, or 3, said carrier vehicle being a spray.

12. The method of claim 1, 2, or 3, the linoleic acid being in the carrier vehicle in microencapsulated form.

* * * * *